United States Patent [19]

Brown et al.

[11] 4,043,334
[45] Aug. 23, 1977

[54] SELF RIGHTING SYRINGE PROTECTOR

[75] Inventors: Tony Ray Brown, Northridge; Leonard Sarkis Neresian, Canoga Park, both of Calif.

[73] Assignee: American Hospital Supply Corporation, Evanston, Ill.

[21] Appl. No.: 700,901

[22] Filed: June 29, 1976

[51] Int. Cl.² .............................................. A61M 5/00
[52] U.S. Cl. .................................. 128/215; 128/218 R
[58] Field of Search ............... 128/215, 218 R, 218 N, 128/218 NV, 220, 221, 261, 260, 239, 2 F; 215/364

[56] References Cited

U.S. PATENT DOCUMENTS

| 3,128,896 | 4/1964 | Schnier | 215/364 |
| 3,344,786 | 10/1967 | Berg et al. | 128/215 |
| 3,900,124 | 8/1975 | Marcel | 215/364 |
| 3,937,211 | 2/1976 | Merten | 128/2 F |

FOREIGN PATENT DOCUMENTS

| 536,756 | 12/1955 | Italy | 215/364 |

Primary Examiner—John D. Yasko
Attorney, Agent, or Firm—Larry N. Barger

[57] ABSTRACT

A cap for closing off a forward end of a hypodermic syringe. This cap has a bulbous rocker joined to a tubular coupler. The bulbous rocker has a center of gravity at a location causing the rocker to orient the tubular coupler in a predetermined upward direction when the protector is placed on a flat horizontal supporting surface. Thus, a series of these self righting protectors can be randomly oriented on a flat horizontal surface, and they automatically will point their tubular connectors in an upward direction.

14 Claims, 5 Drawing Figures

SELF RIGHTING SYRINGE PROTECTOR

BACKGROUND OF THE INVENTION

In hospital pharmacies, the pharmacist often fills hypodermic syringes for use by doctors and nurses on the various hospital floors. Many times needles are not attached until immediately prior to use, the particular needle size required on the syringe is not known, or the particular use does not require a needle. The latter use might include injecting medication into a female Luer adapter of a tube used during surgery.

After the pharmacist has filled such a syringe as described above, he places a cap or protector over the front end of the syringe to prevent leakage and contamination. In the past, small rubber or plastic caps have been used which fit over a male tapered adapter on the syringe's forward end.

There had been a problem with these previous syringe caps or protectors because they were small and difficult to handle. Some pharmacists preferred to manually orient each of these syringe protectors so a tubular coupler is pointed upwardly and then "spike" the syringe to the protectors. This "spiking" involves pushing the syringe tip downwardly into the protector, which is supported on a flat horizontal surface, until the protector is wedged onto the syringe tip. This step of preorienting the syringe protector was time consuming for the pharmacist.

SUMMARY OF THE INVENTION

This invention overcomes the above problem of orienting syringe protectors with a "self orienting" protector. This self orienting protector has a bulbous rocker section connected to a tubular coupler. The bulbous rocker section has its center of gravity located in a particular position so that the rocket portion automatically orients the tubular adapter to an upward position. Thus, a series of protectors of this invention can be placed on a flat horizontal surface and randomly oriented. They will then automatically rock to a position where their tubular couplings are all pointed in a uniform upward direction.

DETAILED DESCRIPTION

Figure 1:
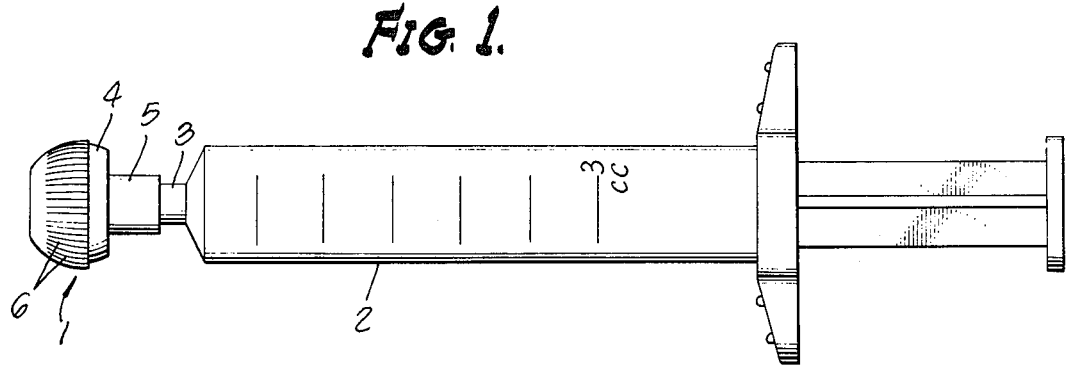
FIG. 1 is a front elevational view of the syringe protector connected to a typical hypodermic syringe in a first embodiment where the syringe has no Luer-lock collar.

FIG. 1 shows the self righting protector, shown generically as 1, connected to a conventional hypodermic syringe 2. It is noted in FIG. 1 that hypodermic syringe 2 has a tapered male adapter wedged into the self righting protector. The protector includes a bulbous rocker 4 that is joined to a tubular coupler 5. Preferably, the external surface of the bulbous rocker is roughened as by ribs 6. These ribs help the nurse or physician twist the protector relative to the syringe to break loose the wedge fit between adapter 3 of the syringe and tubular coupler of the protector.

Figure 2:
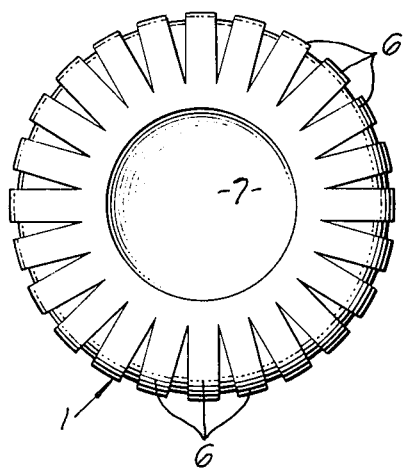
FIG. 2 is an enlarged left end elevatioanl view of FIG. 1.

The enlarged left end view of FIG. 2 shows more detail of the ribs 6, as well as the location of a central dished base portion 7.

Figure 3:
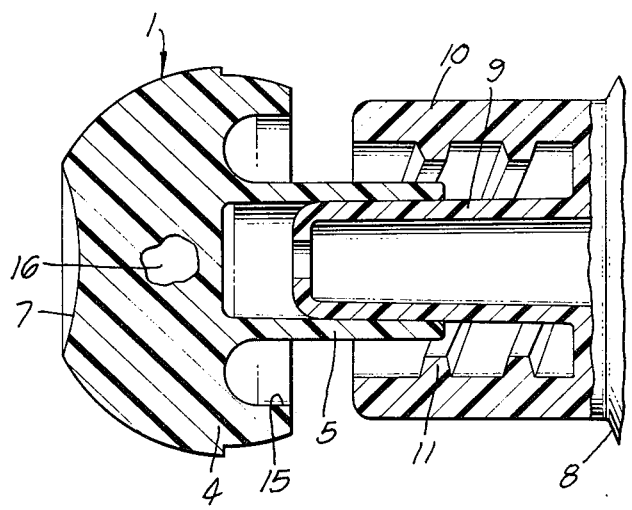
FIG. 3 is a sectional view of the self righting protector of this invention connected to a syringe in a second embodiment of the invention, and this syringe has a Luer-lock collar.

In FIG. 3, the self righting protector is connected to a hypodermic syringe 8 that includes both a tapered male adapter 9 and an internally threaded Luer-lock collar 10. It is preferred that the tubular coupler 5 have no laterally protruding ears to engage with threads 11 of Luer-lock collar 10. It is been found easier to "spike" a syringe with Luer-lock collar to the protector when there are no intermeshing ears on the protector. The lack of intermeshing ears also aids in easy removal of the protector from such syringe with Luer-lock collar. However, it is understood that conventional lateral ears could be included on tubular adapter 5 if desired.

Figure 4:
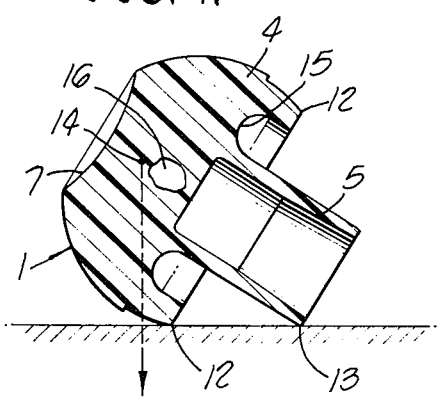
FIG. 4 is a sectional view of the self righting protector showing the position of its center of gravity prior to self righting itself.
Figure 5:
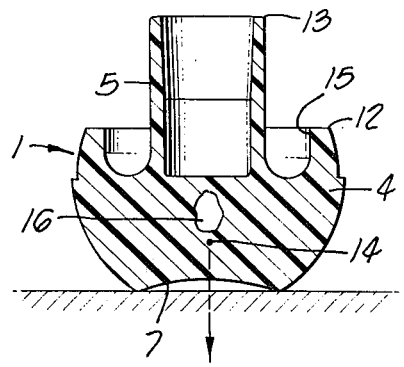
FIG. 5 is a sectional view of the self righting protector after it has been self righted on its base.

FIG. 4 shows a sectional view of a self righting protector that has been randomly disposed on a flat horizontal surface and is resting on an annular pivot edge 12, which is shown both at the upper and lower portions of FIG. 4. This protector is also resting on a forward edge 13 of tubular coupler 5. Because of the location of the protector's center of gravity at 14, the downward force from the center of gravity causes the adapter to rock about annular edge 12 until the protector comes to rest in the position shown in FIG. 5.

The precise location of the protector's center of gravity should be as close as possible to the dished base section 7. An annular groove 15 helps in displacing the center of gravity closer to dished base section 7.

The protector is preferably injection molded of a polypropylene thermoplastic which is very compatible with numerous drugs. During the injection molding process, sometimes a small trapped air bubble 16 will form in the protector. This can effect the precise location of the center of gravity, but has been found to not materially affect the self righting feature of the protector when the bubble is very small. Preferably, in a protector with a bulbous rocker having a diameter of 0.500 inch (12.700 millimeters), the bubble would be less than 0.03 cc.

In the above description of this invention, specific examples have been used to describe the invention. However, it is understood by those skilled in the art that certain modifications can be made to these examples without departing from the spirit and scope of the invention.

We claim:

1. A self righting protector for a hypodermic syringe or the like comprising: a bulbous rocker having a base section; a connector joined to this rocker, said connector having an internally tapered section to wedgingly receive a tapered syringe tip or the like; and said rocker has a center of gravity adjacent its base section to orient the connector in an upward direction when the protector is on a flat horizontal surface, whereby a series of self righting protectors will be uniformly oriented.

2. A protector as set forth in claim 1, wherein the bulbous rocker is generally hemispherical in shape.

3. A protector as set forth in claim 1, wherein the base section has circumferential support means for stabilizing the protector after the bulbous portion has oriented the connector in its upward position.

4. A protector as set forth in claim 3, wherein the base section has a recessed dished section.

5. A protector as set forth in claim 1, wherein the connector has a tubular coupler for attaching to a syringe adapter.

6. A protector as set forth in claim 5, wherein the tubular coupler extends beyond an upper end of the bulbous rocker.

7. A protector as set forth in claim 5, wherein the bulbous rocker has an annular groove surrounding the tubular coupler.

8. A protector as set forth in claim 1, wherein the bulbous rocker has a roughened surface for improved gripping.

9. A protector as set forth in claim 8, wherein the roughened surface includes a series of ribs.

10. A protector as set forth in claim 1, wherein the bulbous rocker has an upper portion with an annular pivot edge, and when said protector is resting on a flat horizontal surface and contacting the surface with its annular pivot edge and the connector, the protector's center of gravity is located beyond the contact point of the annular pivot edge and connector, whereby the center of gravity acts to rock the protector to orient the connector in an upward direction.

11. A protector as set forth in claim 1, wherein the bulbous rocker and connector are a one-piece unit of thermoplastic material.

12. A protector as set forth in claim 11, wherein the protector is of a polypropylene thermoplastic.

13. A capped syringe comprising: a hypodermic syringe having a tapered male adapter at its forward end; a self righting cap having a bulbous rocker section joined to a tubular coupler, said tubular coupler wedgingly fitted to the syring's adapter; said protector having a base section at an opposite end from the tubular coupler, and the protector has a center of gravity located sufficiently close to the base so the protector will orient the tubular coupler in an upright direction when such protector is removed from the syringe and placed on a flat horizontal surface.

14. A capped syringe as set forth in claim 13, wherein the syringe has an internally threaded Luer-lock collar, and the tubular coupler is spaced from and free of engagement with the internally threaded Luer-lock collar.

* * * * *